United States Patent [19]

Colomb, Jr. et al.

[11] 3,966,797

[45] June 29, 1976

[54] DINORBORNENES

[75] Inventors: Henry Octave Colomb, Jr.; David John Trecker, both of South Charleston; Thomas Kemper Brotherton, Charleston, all of W. Va.

[73] Assignee: Union Carbide Corporation, New York, N.Y.

[22] Filed: May 26, 1971

[21] Appl. No.: 147,224

Related U.S. Application Data

[62] Division of Ser. No. 759,759, Sept. 13, 1968, Pat. No. 3,658,669.

[52] U.S. Cl. .............................................. 260/484 A

[51] Int. Cl.$^2$ .......................................... C07C 69/66

[58] Field of Search .................... 260/484 A, 468 E

*Primary Examiner*—Lorraine A. Weinberger

*Assistant Examiner*—P. J. Killos

*Attorney, Agent, or Firm*—Francis M. Fazio

[57] ABSTRACT

Dinorbornene compounds, many of them novel, have been found to form polymers having a ladder structure. The dinorbornene compounds and dinorbornene polymers with other polymers such as the polyolefins, vinyl polymers, acrylic polymers, polyesters, polyamides, polyethers, polyureas, polyurethanes, natural polymers, etc., are readily crosslinked by irradiation.

3 Claims, No Drawings

DINORBORENES

This application is a division of Ser. No. 759,759; filed Sept. 13, 1968, now U.S. Pat. No. 3,658,669, issued Apr. 25, 1972.

This invention relates to dinorbornenes, polymers and copolymers thereof, and blends thereof with other polymer compositions. More particularly, it is concerned with certain novel dinorbornene compounds, the ladder polymers thereof and to blends of the dinorbornenyl compounds with other polymers whereby a readily crosslinkable composition is obtained. As used in this specification, the term polymer encompasses the homopolymers and copolymers of two or more polymerizable monomers.

Many dinorbornenyl compounds have been disclosed in the prior art. In this regard, attention is directed to U.s. Pat. Nos. 3,187,015; 3,030,424; 2,908,712; 2,867,564; 2,421,597; German Pat. No. 945,391; Belgium Pat. No. 633,876; Chemical Abstracts, Vol. 62, 14513g; Chemical Abstracts, Vol. 62, 14514g; Chemical Abstracts, Vol. 55, 27225; J. Am. Chem. Soc., Vol. 85, page 1155; and Chemistry and Industry, London, 20 (1960). These references disclose procedures by which dinorbornenyl compounds can be produced and as is evident from the large number of publications available those skilled in the art can readily produce any desired dinorbornene compound by any one of the known procedures even though it may be a novel dinorbornene compound. It has now been found that the dinorbornene compounds can be polymerized to form so-called ladder polymers. It has also been found that the dinorbornene compounds can be blended with other polymers to obtain readily crosslinkable compositions, and that said compositions can be cured by irradiation.

Any of the general compounding methods for rubbers and plastics may be used to produce the blend of the dinorbornenyl compound with the polymer. Some examples of compounding methods are milling, kneading, masticating, mixer-extruding, tumbling, blending, mulling and mixing. Other more specific methods may also be used to incorporate the dinorbornenyl compound into the polymer such as impregnation, coating, coprecipitation or codeposition from a common solvent and dissolution. All of these procedures are known to those skilled in the art.

Crosslinking of the blends is induced by radiation. Two types of radiation are suitable, ionizing radiation, either particulate or non-particulate, and nonionizing radiation. As a suitable source of particulate radiation, one can use any source which emits electrons or charged nuclei. Particle radiation can be generated from electron accelerators such as the Van de Graaff, resonance transformers, linear accelerators, insulating core transformers, radioactive elements such as cobalt 60, strontium 90, etc. As a suitable source of non-particle ionizing radiation, one can use any source which emits radiation in the range of from about $10^{-3}$ Angstroms, to about 2000 Angstroms, preferably from about $5\times10^{-3}$ Angstroms to about 1 Angstrom. Suitable sources are vacuum ultraviolet lamps, such as xenon or krypton arcs, and radioactive elements such as cesium-137, strontium-90, and cobalt-60. The nuclear reactors are also known to be a useful source of radiation. As a suitable source of nonionizing radiation, one can use any source which emits radiation of from about 2000 Angstroms to about 8000 Angstroms, preferably from about 2500 Angstroms to about 4500 Angstroms. Suitable sources are mercury arcs, carbon arcs, tungsten filament lamps, xenon arcs, krypton arcs, sunlamps, lasers, and the like. All of these devices and sources are well known in the art and those familiar with the technology are fully aware of the manner in which the radiation is generated and the precautions to be exercised in its use.

As is known, irradiation of a polymer with a Van de Graaff accelerator is generally completed in a matter of seconds, even at the highest megarad dosages used in the examples herein. This is to be compared to irradiation periods of hours when light from a mercury arc is the source of energy.

The ionizing radiation dosage necessary to effect crosslinking will vary depending upon the particular polymer that is undergoing radiation, the extent of crosslinking desired, the number of crosslinkable sites available and the molecular weight of the starting polymer. The total dosage will be from about $10^3$ rads to $10^8$ rads, preferably from $5 \times 10^3$ rads to $10^7$ rads. A rad is 100 ergs of ionizing energy absorbed per gram of material being irradiated.

The irradiation is carried out at a temperature below the decomposition temperature of the crosslinkable blend undergoing treatment; generally it is from about 0°C. to about 150°C. Any temperature that does not permanently degrade the polymers can be used.

To prevent undesirable side reactions, an inert atmosphere is preferable present; however, this is not critical and the reaction can be carried out under ambient atmospheric conditions.

The suitable dinorbornenes are those compounds represented by the general formula:

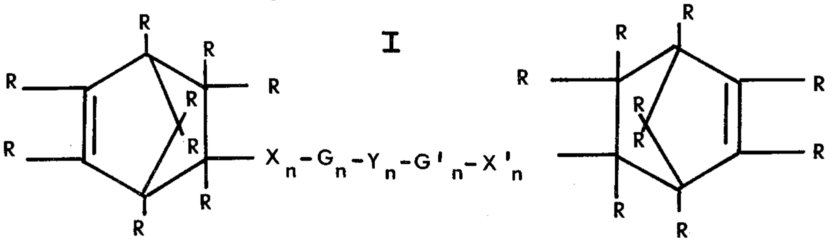

I wherein $n$ is 0 or 1 and R can be hydrogen; halogen; alkyl of from 1 to about 8 carbon atoms, such as methyl, ethyl, propyl, butyl, isobutyl, tertiary butyl, pentyl, neopentyl, isopentyl, hexyl, 2-methylpentyl, neohexyl, heptyl, octyl, 2-ethylhexyl, cyclopentyl cyclohexyl, methylcyclopentyl, dimethylcyclopentyl and the like; alkenyl of from 2 to about 8 carbon atoms, such as ethenyl, propenyl, butenyl, isobutenyl, butadienyl, pentenyl, hexenyl, heptenyl, octenyl, the branched isomers thereof, and the like; aryl of from 6 to about 16 carbon atoms, such as phenyl, naphthyl, anthracyl, tolyl, xylyl, benzyl, phenethyl, biphenyl, naphthal, methylnaphthyl, and the like. Preferably, not more than two of the R groups in the molecule are aryl groups. The symbols X, X′ and Y can be the same or different divalent groups and can be divalent alkylene of from 1 to about 8 carbon atoms, such as methylene, ethylene, propylene, butylene, pentylene, hexylene, heptylene, octylene, cyclopentylene, cyclohexylene, methylcyclopentylene, the branched isomers thereof, and the like; mono or poly unsaturated divalent alkenylene of from 2 to about 8 carbon atoms, such as ethenylene, propenylene, butenylene, butadienylene, pentenylene, pentadienylene, hexenylene, hexadienylene, heptenylene, heptadienylene, octenylene, octadienylene, cyclopentenylene, cyclohexenylene, the branched isomers thereof, and the like; divalent arylene of from 6 to about 16 carbon atoms, such as phenylene, naphthylene, anthracylene, tolylene, xylylene, biphenylene, methylnaphthylene, propylnaphthylene, and the like; divalent poly(oxyalkylene) having from 2 to about 5,000 oxyalkylene units in the chain wherein the oxyalkylene unit has from 2 to about 4 carbon atoms, such as oxyethylene, oxypropylene, 2-oxypropylene, oxybutylene, and the like; divalent poly(alkylenecarbonyloxy) having from 3 to about 5,000 alkylenecarbonyloxy units $-C_xH_{2x}COO-$, in the chain wherein the alkylenecarbonyloxy unit has from 3 to about 12 carbon atoms, such as poly(caprolactone), poly(butyrolactone), poly(propiolactone), poly(valerolactone), and the like. The symbols G and G' can be the same or different divalent groups and can be carbonyloxy

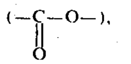

oxycarbonyl

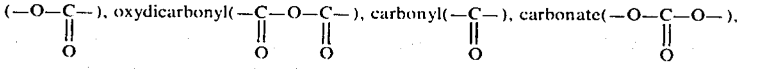

oxydicarbonyl, carbonyl, carbonate,

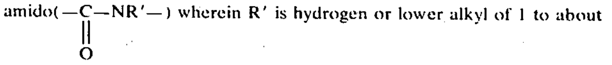

amido wherein R' is hydrogen or lower alkyl of 1 to about 5 carbon atoms,

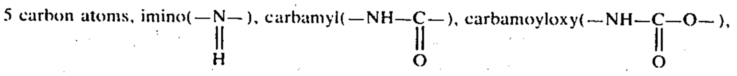

imino, carbamyl, carbamoyloxy,

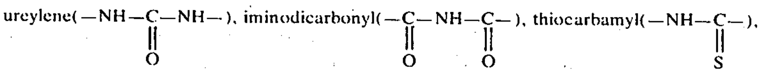

ureylene, iminodicarbonyl, thiocarbamyl,

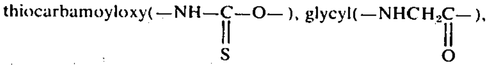

thiocarbamoyloxy, glycyl, oxy(—O—), thio(—S—), sulfoxy(—SO—), sulfonyl($-SO_2-$), and sulfite($-SO_3-$).

The following formulas are subgeneric to general formula I. In the subgeneric formulas the term BCH represents the bicycloheptenyl group

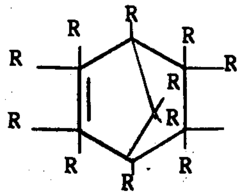

These subgeneric formulas do not encompass all the possible subgenuses of formula I but only a few thereof. Also, only one half of the structure is illustrated; thus, the X' and G' groups can be the same as X and G to give the symmetrical compounds, or different to give the unsymmetrical compounds. From this description one skilled in the art can readily write other subgeneric formulas.

I-A: [BCH—$X_n$—$G_n$—poly(alkylenecarbonyloxy) $]_{\frac{1}{2}}$ O

I-B: [BCH—$X_n$—$G_n$ $]_{\frac{1}{2}}$ poly(alkylenecarbonyloxy)

I-C: [BCH—$X_n$—$G_n$ $]_{\frac{1}{2}}$ poly(alkyleneoxy)

I-D: [BCH—$X_n$—$G_n$ $]_{\frac{1}{2}}$ divalent alkylene

I-Da: [BCH—$X_n$—G $]_{\frac{1}{2}}$ divalent alkylene

I-E: [BCH—$X_n$—$G_n$ $]_{\frac{1}{2}}$ divalent arylene

I-Ea: [BCH—$X_n$—G $]_{\frac{1}{2}}$ divalent arylene

I-F: [BCH—$X_n$—$G_n$ $]_{\frac{1}{2}}$ divalent alkenylene

I-G: [BCH—$X_n$—$G_n$ $]_{\frac{1}{2}}$ divalent cycloalkenylene

I-H: [BCH—$X_n$—$G_n$ $]_{\frac{1}{2}}$ divalent cycloalkylene

I-I: [BCH—$X_n$—OOC$]_2Y_n$

I-J: 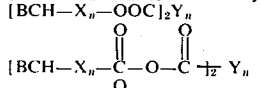

I-K: 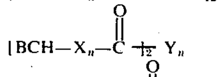

I-L: 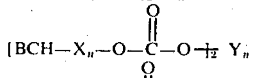

I-M: 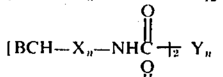

I-N: 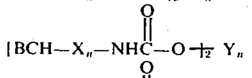

I-O: 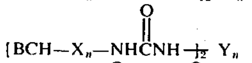

I-P: 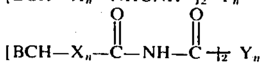

I-Q: 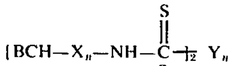

I-R: 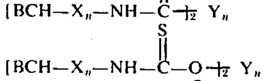

I-S: 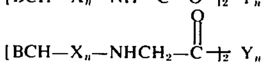

The following table lists formulas of specific dinorbornene compounds falling within the scope of the general formula. This tabulation of compounds is illustrative only and is not to be considered a complete tabulation of all the suitable compounds. In the tabulation the norbornenyl or BCH bicyclo structure is not portrayed; the table sets forth that portion represented by the -$X_n$-$G_n$-$Y_n$-$G'_n$-$X'_n$- section of the compounds of the formula Norb-$X_n$-$G_n$-$Y_n$-$G'_n$-$X'_n$Norb, wherein "Norb" represents the substituted or unsubstituted nobornenyl moiety present in general formula I. In the following tabulation the units are connected in the order shown to the norbornenyl nuclei. The simplest compound is dinorbornene, wherein all of the *n*'s are zero, this compound is not shown in the following tabulation but it is within the scope of this invention.

| —$X_n$— | —$G_n$— | —$Y_n$— | —$G_n'$— | —$X_n'$— |
|---|---|---|---|---|
| —$CH_2$— | — | — | — | — |
| —$C_3H_6$— | — | — | — | — |
| —$C_4H_8$— | — | — | — | — |
| —$C_8H_{16}$— | — | — | — | — |
| 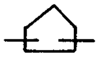 | — | — | — | — |
| —CH=CH— | — | — | — | — |
| —$CH_2C(CH_3)$=CH— | — | — | — | — |
| —CH=CHCH=CH— | — | — | — | — |
| 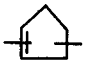 | — | — | — | — |
| 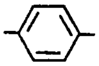 | — | — | — | — |
| 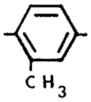 | — | — | — | — |
| 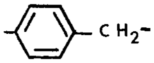 | — | — | — | — |
| 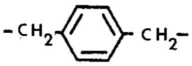 | — | — | — | — |
| —$CH_2$— | —OOC— | — | — | — |
| —$C_2H_4$— | —COO— | — | — | |
| —$CH_2$— | —C(=O)—O—C(=O)— | — | — | — |
| —$C_3H_6$— | —C(=O)— | — | — | — |
| —$CH_2$— | —C(=O)—NH— | — | — | — |
| —$C_4H_8$— | —NH— | — | — | — |
| —CH=CH— | —NHC(=O)— | — | — | — |
| —$CH_2$— | —NHC(=O)—O— | — | — | — |
| —$CH_2$— | —NHC(=O)NH— | — | — | — |
| —$CH_2$— | —NHC(=S)— | — | — | — |
| —$CH_2$— | —NHC(=S)—O | — | — | — |
| —$C_3H_6$— | —$NHCH_2C$(=O)— | — | — | — |
| —$C_2H_4$— | —O— | — | — | — |
| — | —S— | — | — | — |
| —$C_4H_8$— | —S— | — | — | — |
| —$CH_2$— | —SO— | — | — | — |
| —$CH_2$— | —$SO_2$— | — | — | — |
| —$C_2H_4$— | —$SO_3$— | — | — | — |
| —$CH_2$— | —O—C(=O)—O— | —$CH_2$— | — | — |
| —$C_2H_4$— | —O— | —$C_2H_4$— | — | — |
| —$CH_2$— | —$SO_3$— | —$CH_2$— | — | — |
| -iso$C_3H_6$— | —NH— | —$CH_2$— | — | — |
| —$CH_2$— | —O— | —$CH_2$— | — | — |
| —$C_3H_6$— | —O— | —$C_3H_6$— | — | — |
| —$CH_2$— | —NHC(=O)NH— | —$CH_2$— | — | — |
| —$CH_2$— | —C(=O)—O— | —$CH_2$— | — | — |

-continued

| $-X_n-$ | $-G_n-$ | $-Y_n-$ | $-G_n'-$ | $-X_n'-$ |
|---|---|---|---|---|
| — | $-C(O)-O-C(O)-$ | — | — | — |
| — | —COO— | — | — | — |
| $-CH_2-$ | —OOC— | 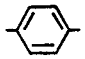 | —COO— | $-CH_2-$ |
| $-CH_2-$ | —NHC(O)—O— | 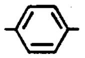 | —O—C(O)NH— | $-CH_2-$ |
| — | —COO— | 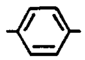 | —OOC— | — |
| — | —COO— | $-C_4H_8-$ | —OOC— | — |
| — | —C(O)—NH— | $-C_6H_{12}-$ | —HN—C(O)— | — |
| $-CH_2-$ | —NHC(O)—O— | $-C_2H_4-$ | —O—C(O)NH— | $-CH_2-$ |
| — | —C(O)—NH— | 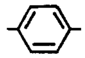 | —HNC(O)— | — |
| $-CH_2-$ | —S— | 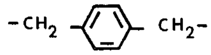 | —S— | — |
| — | —COO— | 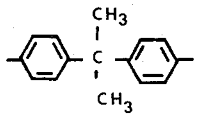 | —OOC— | — |
| $-CH_2-$ | —NHC(O)—O— | $-(CH_2CH_2O)_m-$ m = 4, 10, 25, or 100 | —O—C(O)NH— | $-CH_2-$ |
| $-CH_2-$ | —NHC(O)—O— | $-(C_5H_{10}COO)_p-(C_2H_4O)_q-$ p = 2–100; q = 1–4 | —C(O)NH— | $-CH_2-$ |
| — | $-C(O)-N(CH_3)-$ | — | —C(O)— | — |
| — | —O— | — | — | — |
| — | $-SO_2-$ | — | — | — |
| $-CH_2-$ | —OOC— | —CH=CH— | —COO— | —CH— |
| — | —C(O)— | — | — | — |
| — | —COO— | — | —OOC— | — |
| — | —NHC(O)NH— | — | — | — |
| — | —C(O)— | — | —C(O)— | — |
| $-CH_2-$ | —O—C(O)NH— | 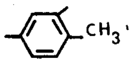 | —NHC(O)—O— | $-CH_2-$ |
| — | —COO— | $-C_2H_4-$ | —OOC— | — |
| — | —COO— | 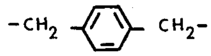 | —OOC— | — |
| $-CH_2-$ | —NHC(O)NH— | $-C_6H_{12}-$ | —NHC(O)NH— | $-CH_2-$ |
| $-CH_2-$ | —OOC— | $-C_4H_8-$ | —COO— | $-CH_2-$ |
| $-CH_2-$ | —O— | 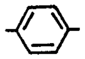 | —O— | $-CH_2-$ |
| $-CH_2-$ | —NHC(O)—O— | $-(CH_2CH(CH_3)O)_m-$ m = 1–80 | —O—C(O)NH— | $-CH_2-$ |

-continued
| $-X_n-$ | $-G_n-$ | $-Y_n-$ | $-G_n'-$ | $-X_n'-$ |
|---|---|---|---|---|
| $-CH_2-$ | —O— | 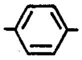 | —O— | — |
Also included, as indicated, are the compounds set forth above wherein the norbornenyl nucleus is substituted; illustrative thereof would be the following
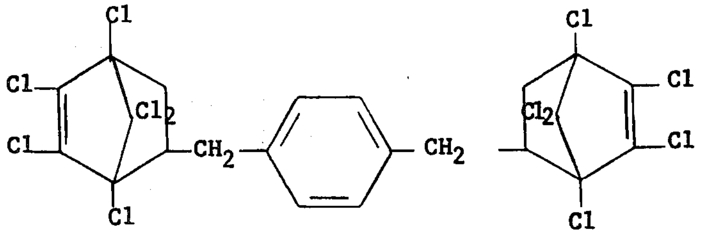
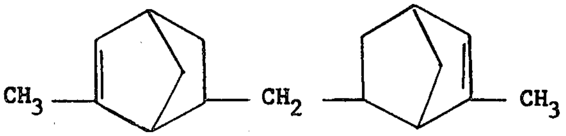
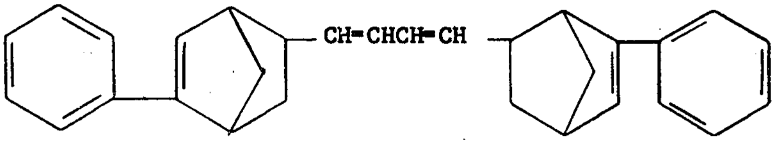
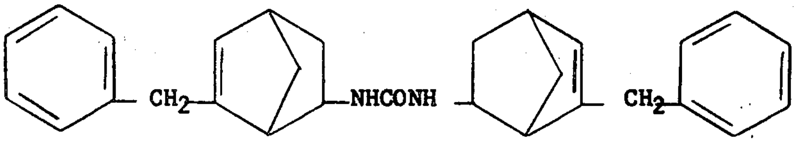
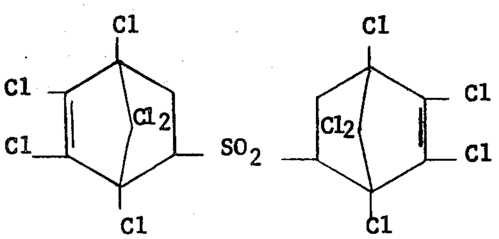
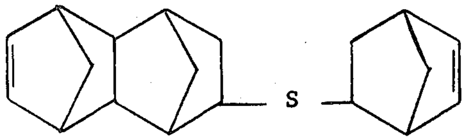
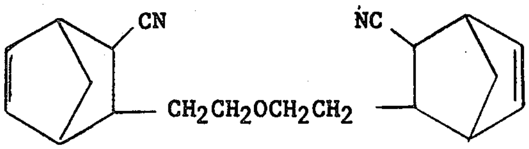
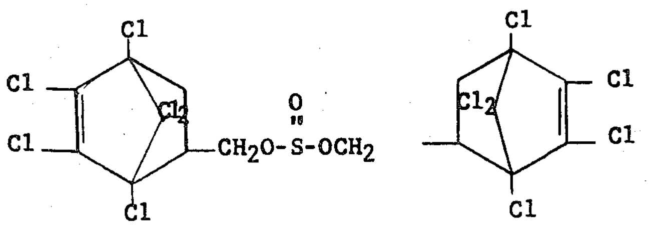
and the like. The important feature of the suitable compounds is that they contain two norbornenyl rings. As mentioned previously, many dinorbornene compounds are known, as are the processes for their production; reference has been made to publications showing some of the known processes. Modifications thereof are readily known and ascertainable to the ordinary skilled organic chemist and such as individual will have no problem determining the manner by which any of the above-listed compounds can be produced and the reactants necessary therefor. Thus, the Diels-Alder condensation of two moles of cyclopentadiene with ethylene glycol diacrylate will produce 5-norbornene-2-ylcarbonyloxyethyl 5-norbornene-2-carboxylate. This compound can also be produced by the reaction of two moles of 5-chlorocarbonylbicyclo[2.2.1-]hept-2-ene with ethylene glycol. The reaction of divinyl sulfone with two moles of cyclopentadiene yields bis(5-norbornen-2-yl)sulfone. The condensation of two moles of bicyclo[2.2.1]hept-2-en-5-aldehyde in the presence of aluminum isopropoxide as catalyst yields 5-norbornen-2-ylmethyl 5-norbornene-2-carboxylate. Reaction of phosgene with 5-hydroxymethylbicyclo[2.2.1]hept-2-ene yields bis(5-norbornen-2-ylmethyl)carbonate. The reaction of 5-chlorocarbonylbicyclo[2.2.1]hept-2-ene with 1,4 -dihydroxybenzene yields 1,4-phenylene is 5-norbornene-2-carboxylate); with 1,4-dihydroxymethylbenzene the product is 1,4-xylylene bis(5-norbornene-2-carboxylate; with 2,2-bis(4-hydroxyphenyl)propane the product is 2,2-bis(4-phenyl)propane bis(5-norbornene-2-carboxylate; with 1,6-hexanediamine the product is 1,6-hexamethylene-N,N'-bis(5-norbornene-2-carboxamide); with p-phenylenediamine the product is1,4-phenylene-N,N'-bis(5-norbornene-2-carboxamide); and with methylamine the product is N-methyliminodicarbonyl bis(5-norborn-2-ene). The reaction of 5-isocyanatomethylbicyclo[2.2.1]hept- 2-ene with ethylene glycol yields ethylene-1,2-bis[N-(5-norbornen-2-ylmethyl)carbamate]; with 1,6-hexanediamine the product is hexamethylene-1,6-N,N'-bis[N-(5-norbornen-2-ylmethyl-)urea]; with water the product is N,N'-bis(5-norbornen-2-ylmethyl)urea; and with 1,4-dihydroxybenzene the product is 1,4 phenylene-bis-[N-(5-norbornen-2-ylmethyl)carbamate]. The reaction of 5-hydroxymethylbicyclo[2.2.1]hept-2-ene with the diacid chloride of terephthalic acid yields di(5-norbornen-2-ylmethyl)-terephthalate; with the diacid chloride of 1,4-hexanedioic acid the product is di(5-norbornen-2-ylmethyl)adipate; with 2,4-diisocyanatotoluene the product is bis(5-norborne-2-ylmethyl) N,N'-(2-methyl-1,4-phenylene)-carbamate; with 1,4-dichlorobenzene the product is phenylene-1,4-dioxybis(5-methyl-2-norbornene); and with 1,6-dichlorohexane the product is hexamethylene-1,6-dioxybis(5-methyl-2-norbornene).

The dinorbornene compounds defined by general formula I can be polymerized together with one or more different polymerizable ethylenically unsaturated monomer. Polymerization can be achieved by employing conventional free radical initiators using known polymerization processes. Representative examples of free radical initiators are, among the peroxides, benzoyl peroxide, acetyl peroxide, diisopropoxy percarbonate, t-butyl peracetate, di-t-butyl peroxide, cumene hydroperoxide, and the like; and, among the azo compounds, azobis isobutyronitrile, azobis(cyclohexane), dimethyl azobis[isobutyrate], and the like. Polymerization temperatures are known to depend on the half-life of the peroxide or azo initiator and generally fall in the range of 50°–200°C., with the most useful temperatures being from about 80°–150°C. These free radical initiated polymerizations occur across the double bond. In some instances, depending upon the conditions used, some crosslinking may occur.

In addition, the dinorbornene compounds can be polymerized alone or in the presence of photosensitizers known to those skilled in the art to catalyze the norbornene dimerization reaction to produce so-called ladder polymers, wherein a cyclobutane ring is formed between two molecules thereof. The ladder polymers are generally produced by light catalysis, i.e. by exposure of the dinorbornene compounds to a light source whereby dimerization of the double bond in the bicycloheptenyl moiety occurs to form the cyclobutane moiety in the molecule:

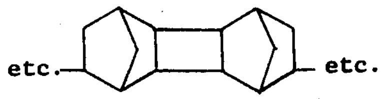

In contrast to the free radical polymerization, these ladder polymers have not shown any evidence of crosslinking.

The ladder polymers produced by the polymerization of the dinorbornene compounds contain units represented by the general formula:

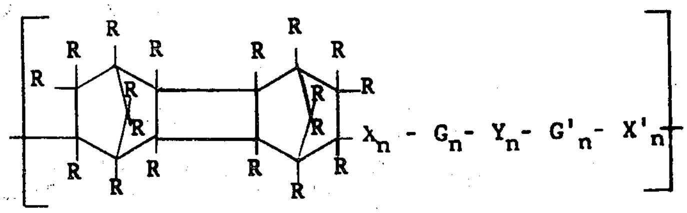

All of the dinorbornene polymers produced can be used to produce molded articles, films, insulation for wires, protective coatings, fibers, and for many other applications in which synthetic polymers are conventionally employed.

In addition, the fused dinorbornene compounds of the general formulas

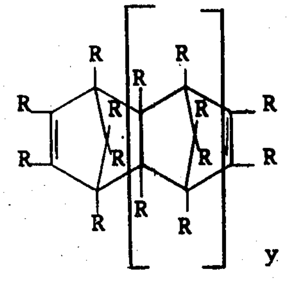

and

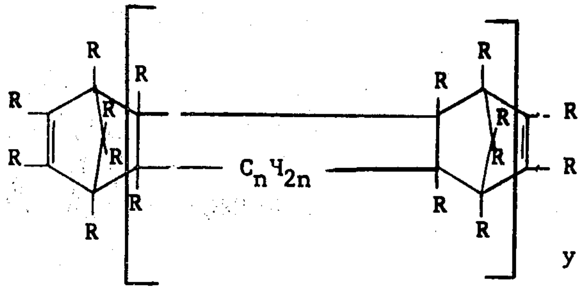

can also be used in this invention. These compounds can contain the same R substituents on the rings that were set forth in formula I, *n* is 0 or 1 and *y* is 1 or 2. Illustrative thereof one can mention tetracyclo[6.2.1.$1^{3,6}$.$0^{2,7}$]dodeca-4,9-diene, 1,8,9,10,11-hexachloro-tetracyclo[6.2.1.$1^{3,6}$.$0^{2,7}$]dodeca-4,9-diene, hexacyclo[10.2.1.$1^{3,10}$.$1^{5,8}$.$0^{2,11}$.$0^{4,9}$]heptadeca-6,13-diene, pentacyclo[8.2.1.$1^{4,7}$.$0^{2,9}$.$0^{3,8}$]tetradeca-5-11-diene, 3,9-dimethylpentacyclo[8.2.1.$1^{4,7}$.$0^{2,9}$.$0^{3,8}$]tetradeca-5,11-diene, octacyclo[14.2.1.$1^{4,13}$.$1^{7,10}$.$0^{2,5}$.$0^{3,14}$.$0^{5,12}$.$0^{6,11}$]heneicosa-8,17-diene, and the like.

The dinorbornene compounds defined by the general formula and the polymers produced therefrom can be blended with other polymers to produce uniform blends that are cured by irradiation, as indicated above. The term polymer as used herein includes the homopolymers and copolymers with one or more copolymerizable monomer. The polymers blended with the dinorbornenes to produce the crosslinkable blends include the olefin polymers and copolymers such as polyethylene, polypropylene, polyisobutene, polybutene, poly(ethylene/propylene), poly(ethylene/butene), poly(ethylene/butadiene), poly(ethylene/norbornadiene), poly(ethylene/propylene/norbornadiene), poly(ethylene/propylene/5-methylenebicyclo[2.2.1-]hept-2-ene), poly(ethylene/propylene/5-ethylidenebicyclo[2.2.1]hept-2-ene), poly(ethylene/vinyl acetate), poly(ethylene/vinyl chloride), poly(ethylene/ethyl acrylate), poly(ethylene/acrylonitrile), poly(ethylene/acrylic acid), poly(ethylene/styrene), poly(ethylene/vinyl ethyl ether), poly(ethylene/vinyl methyl ketone), and the like. The olefin polymers are well known and any such polymer can be used to produce the crosslinkable blend. Also suitable are the vinyl and vinylidene polymers such as poly(vinyl chloride), poly(vinyl bromide), poly(vinylidene chloride), poly(vinyl acetate), poly(vinyl methyl ether), poly(vinyl butyl ether), poly(vinyl methyl ketone), poly(vinyl alcohol), poly(allyl alcohol), polyindene, poly(vinylpyridine), poly(vinylpyrrolidone), and the like. Further, suitable are the acrylic polymers such as poly(acrylic acid), poly(methyl acrylate), poly(ethylacrylate), polyacrylonitrile, polyacrylamide, polyacrolein, and the like. In addition, the polyesters and polyamides such as polycaprolactone, poly(caprolactone/vinyl chloride), poly(ethylene glycol terephthalate), poly(hexamethylene succinate), poly(hexamethylene maleate), poly(hexamethylene carbonate), poly(caprolactam), poly(hexamethylene adipamide), and the like, are useful. The polyethers such as poly(glutardialdehyde), polyethylene oxide, polypropylene oxide, copolymers of ethylene oxide and propylene oxide with starters containing two or more reactive hydrogen atoms such as the mixed copolymer using ethylene glycol, glycerol, sucrose, etc., as the starter. It was noted, however, that polyformaldehyde and polyacetaldehyde did not crosslink. Also suitable are the polyureas and polyurethanes, as well as the natural and modified natural polymers such as gutta percha, cellulose, methyl cellulose, starch, silk, wool, and the like, and the siloxane polymers and copolymers. One can use a single polymer in the blend with the dinorbornenyl compound or two or more polymers. In producing a blend using two or more polymers with the dinorbornene compound, the concentration of each polymer in the final blend is not critical and can be varied at the will of the individual from 0.01 to 99.99 parts of a first polymer with one or more other polymers.

In producing the blends, the concentration of the dinorbornene compound therein can vary from about 0.01 to about 80 weight per cent of the total blend; it is preferably from about 0.1 to about 10 weight per cent. The difference consists of the polymer plus modifiers and fillers, if the latter are present. If desired, an inert solvent can be used to facilitate blending. Suitable solvents will depend upon the particular polymers and dinorbornene compounds involved. Included are water, methanol, ethanol, butanol, benzene, toluene, ethylbenzene, chlorobenzene, hexane, dimethyl sulfoxide, dimethyl formamide, diethyl ether, ethylene glycol mono- and di-ethyl ethers, diethylene glycol mono- and di-methyl ethers, acetone, methyl ethyl ketone, and the like. The concentration of the solvent is not critical since its sole function is as a mixing aid. Latices can also be produced.

A photosensitizer can be added to increase the rate of crosslinking when one uses a source of non-ionizing radiation, if one wishes to do so. This is optional and any of the known photosensitizers can be used, such as acetophenone, benzophenone, acetone, methyl ethyl ketone, cyclohexanone, benzladehyde, benzene, p-dichlorobenzene, benzoic acid, pyrazine, benzoin, triphenylene, benzil, biacetyl, Michler's ketone, quinoline, 2-acetonaphthone, 1-naphthaldehyde, xanthone, and the like. The concentration of the photosensitizer can vary from about 0.01 mole per cent or less to about 2 mole per cent or more based on the dinorbornenyl compound present. Preferred concentrations are from about 0.1 mole per cent to about 1 mole per cent.

The blends can be applied as finishes on wood, paper, glass, plastics, metals, fibers fabrics, and other materials and then cured. These blends can be used as coatings or impregnants. They also find utility as insulation materials and cable coatings thus enabling the manufacturer to apply the insulation without difficulty and subsequently irradiate it to a tough durable product. The use of these compositions offers many technical and processing advantages, for example, milder conditions for curing, the addition of the crosslinking dinorbornene compounds by a simple mixing process, ease of control of the curing process by merely controlling the type of irradiation and the duration of the radiation period, the absence of catalyst contaminants, and the like.

The following examples further serve to illustrate the invention. The examples are divided into three Sections; Section A relates to the dinorbornene compounds per se, Section B relates to the polymers thereof, and Section C relates to blends of the dinorbornene compounds with other polymers.

SECTION A

EXAMPLE 1

A mixture was prepared containing 14.9 grams of 5-isocyanatomethylbicyclo[2.2.1]hept-2-ene, 100 grams of a polycaprolactone diol having an average molecular weight of about 2,000 (produced according to U.S. Pat. No. 3,169,945) and one drop of dibutyltin dilaurate. The mixture was heated under a nitrogen atmosphere at about 90°C. for about 5 hours and then allowed to cool. The carbamate produced was a waxy solid having a reduced viscosity at 30°C. of 0.13 when measured from a 0.5 per cent solution in chloroform. The structure of the carbamate was confirmed by infrared analysis as:

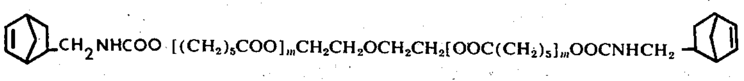

wherein the total number of m groups present is an average of about 16.6. Microanalytical data further confirmed that the carbamate was produced.

Microanalysis:

Calc. for $C_{121.6}H_{198}O_{38.2}N_2$ : C, 63.6; H, 8.7; N, 1.2

Found: C, 63.8; H, 8.7; N, 1.3

EXAMPLE 2

A mixture was prepared containing 13.2 grams of 5-isocyanatomethylbicyclo[2.2.1]hept-2-ene, 17.4 grams of polyethylene glycol having an average molecular weight of about 400 and one drop of dibutyltin dilaurate. This was stirred at room temperature for 48 hours to produce the carbamate of the formula:

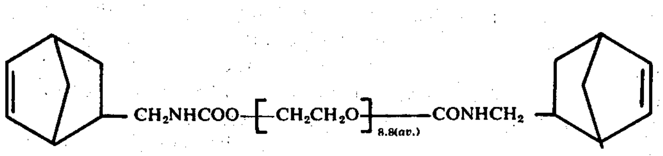

The carbamate was a viscous, clear liquid having a reduced viscosity at 30°C. of 0.05 when measured from a 0.5 per cent solution in chloroform. Microanalytical data further confirmed that the carbamate was produced.

Microanalysis:

Calc. for $C_{35.5}H_{59}O_{11.8}N_2$ : C, 60.8; H, 8.4; N, 4.0

Found : C, 60.8; H, 8.6; N, 4.0

EXAMPLE 3

To a mixture of 19.8 grams of polyethylene glycol having an average molecular weight of about 200 and one drop of dibutylin dilaurate there was added in a dropwise manner 31.4 grams of 5-isocyanatomethylbicyclo[2.2.1]hept-2-ene at a temperature of 80°C. to 90°C. After addition was complete, the mixture was stirred at that temperature for a total reaction time of two hours and then stripped at 30°C. to 50°C. at a pressure of 2 to 6 mm. of mercury on a rotary evaporator. The carbamate produced was a clear, viscous liquid of the formula:

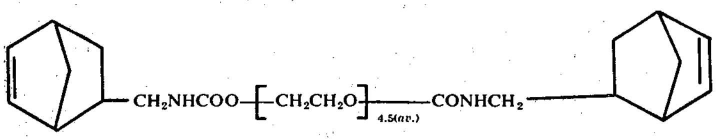

EXAMPLE 4

In a manner similar to that described in Example 3, 49.1 grams of polyethylene glycol having an average molecular weight of about 1,000 and 15.7 grams of 5-isocyanatomethylbicyclo[2.2.1]hept-2-ene were reacted to produce the carbamate of the formula:

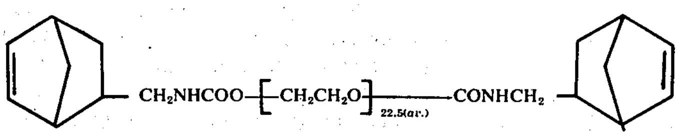

The carbamate was a semi-fluid wax paste.

EXAMPLE 5

In a manner similar to that described in Example 3, 143.6 grams of polyethylene glycol having an average molecular weight of about 4000 and 15.7 grams of 5-isocyanatomethylbicyclo[2.2.1]hept-2-ene were reacted to produce a waxy, solid carbamate of the formula:

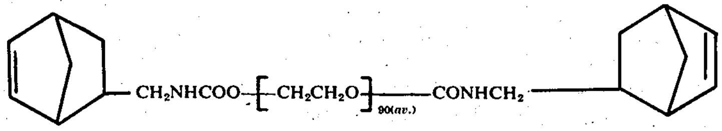

EXAMPLE 6

In a manner similar to that described in Example 3, 49.6 grams of polypropylene glycol having an average molecular weight of about 1,000 and 15.7 grams of 5-isocyanatomethylbicyclo[2.2.1]hept-2-ene were reacted to produce a clear, viscous liquid carbamate of the formula:

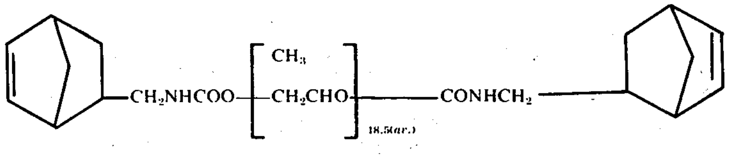

EXAMPLE 7

A solution was prepared containing 47.3 grams of 1,6-hexanediol, 65 grams of pyridine and 500 ml. of diethyl ether. To the above-solution there was added in a dropwise manner at a temperature of 25° to 30°C. a solution of 125.3 grams of 5-chloroformylicyclo[2.2.1-]hept-2-ene in 100 ml. of diethyl ether. The reaction mixture was stirred overnight at room temperature and then filtered to remove the precipitated pyridine hydrochloride. The filtrate was washed four times with water. The washed organic solution was dried over anhydrous magnesium sulfate, filtered and fractionally distilled to remove the ether. The diester produced weighed 122.3 grams; its structure was confirmed by infrared analysis and microanalysis as having the formula:

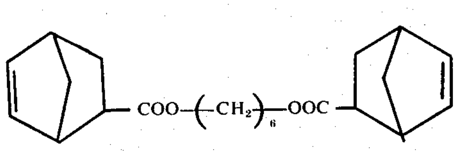

Microanalysis:
Calc. for $C_{20}H_{30}O_4$: C, 73.7; H, 8.4
Found : C, 73.4; H, 8.7

EXAMPLE 8

A solution of 47.3 grams of 1,6-hexanediol, 122.2 grams of 5-isocyanatomethylbicyclo[2.2.1]hept-2-ene and 350 ml. of toluene was refluxed overnight. The reaction mixture was cooled in an ice bath and the crystals filtered. The crystals were washed with fresh toluene and dried at 55°C. under vacuum. The white crystals weighted 142.8 grams and melted at 86°C. to 87°C. The carbamate's structure was confirmed by infrared analysis and corresponded to the formula:

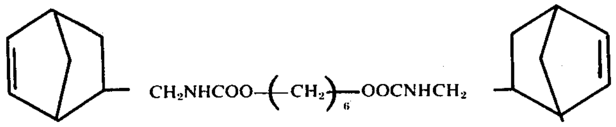

EXAMPLE 9

A solution ob 29.1 grams of 1,6-hexamethylenediamine in 200 ml. of toluene was added all at once to a solution of 74.6 grams of 5-isocyanatomethylbicyclo[2.2.1]hept-2-ene in 300 ml. of toluene and the resulting mixture was stirred at high speed for 30 minutes. After the stirring was stopped, two liquid layers immediately formed. On standing at room temperature the bottom layer crystallized after several hours. The crystals were recovered by filtration, washed with toluene and dried under vacuum at 55°C. The urea weighted 90.5 grams and melted at 109°C. to 111°C. The urea's structure was confirmed by infrared and corresponded to the formula:

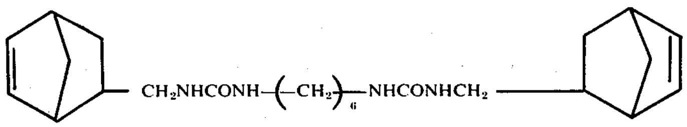

EXAMPLE 10

A solution of 46.5 grams of 1,6-hexamethylenedimine, 53 grams of sodium carbonate and 200 ml. of water was prepared. Five hundred ml. of toluene were added and the two phase mixture was cooled to 2°C. and stirred. A solution of 130 grams of 5-chloroformylbicyclo[2.2.1]hept-2-ene in 100 ml. of toluene was added to cold mixture in one portion with rapid stirring. A white precipitate formed instantaneously and it was filtered, washed with water and dried at 55°C. under vacuum. The amide weighed 68 grams and melted at 150°C. to 151°C. The amide's structure was confirmed by infrared analysis and microanalysis and corresponds to the formula:

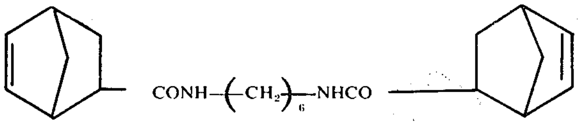

Microanalysis:
Calc. for $C_{22}H_{32}O_{22}N_2$: C, 74.1; H, 9.0; N, 7.9
Found: C, 74.1; H, 9.3; N, 7.9

EXAMPLE 11

A solution of 203 grams of terephthaloyl chloride in 800 ml. of acrylonitrile was prepared in a reaction flask equipped with a stirrer, condenser, dropping funnel and thermometer. A solution of 280 grams of 5-hydroxymethylbicyclo[2.2.1]hept-2-ene in 200 ml. of acrylonitrile was slowly added at 25°C. to 30°C. over a period of about 40 minutes and the mixture was stirred at room temperature for another 3.5 hours. The solvent was removed by vacuum distillation and the residue was heated at 80°C. at about 100 mm. pressure to remove remaining traces of volatile materials. On cooling the ester solidified. The crude di(bicyclo[2.2.1]hept-5-en-2ylmethyl)terephthalate was purified by solution in acetone and reprecipitation by the slow addition of water with vigorous stirring until the cloud point was reached. Continued stirring produced a copious white precipitate that was filtered and dried. The ester melted at 98°C. to 99°C; the structure was confirmed by infrared analysis and microanalysis and corresponds to the formula:

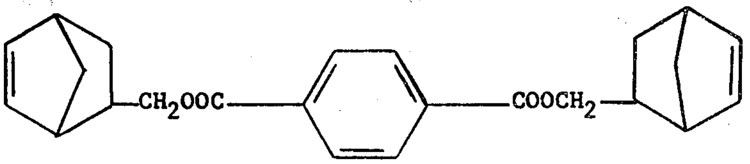

Microanalysis:
Calc. for $C_{24}H_{26}O_4$: C, 76.2; H, 6.9
Found: C, 75.8; H, 6.9

EXAMPLE 12

A solution of 100 grams of a poly-epsilon-caprolactone diol having an average molecular weight of about 10,000 in 300 ml. of benzene was prepared in a reaction vessel equipped with a stirrer, condenser and thermometer. The solution was heated under nitrogen and 50 ml. was distilled to remove traces of water. After cooling to 70°C. and adding two drops of dibutyltin dilaurate, 3.14 grams of 5-isocyanatomethylbicyclo[2.2.1]hept-2-ene were added. The solution was stirred at 70°C. for one-half hour and cooled to room temperature and allowed to stand for 72 hours under the nitrogen atmosphere. The volatiles were distilled at 100°C. at 5 mm. of mercury and the carbamate was recovered as a white, waxy solid weighing 103.4 grams. The structure was confirmed by infrafed analysis as:

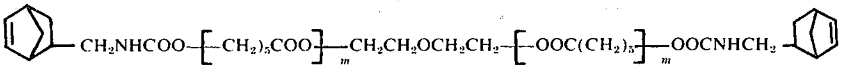

wherein the total number of m groups present is an average of about 83.

SECTION B

EXAMPLE 13

A solution of 9 grams of pentacyclo[8.2.1.1$^{4,7}$.0$^{2,9}$.0$^{3,8}$]tetradeca-5,11-diene and 19 grams of acetophenone, as the photosensitizer, was placed in a Pyrex tube, degassed and sealed. The tube was irradiated with ultraviolet light using a 140 watt mercury arc at a distance of 10 cm. for a period of 20 days. The temperature ranged from 40°C. to 45°C. A solid white polymer was produced that was filtered, washed with acetone and dried. The polymer had a reduced viscosity of 0.01 at 30°C. when measured from a 0.1 per cent solution in chloroform. A film was produced from the polymer whose structure formula is:

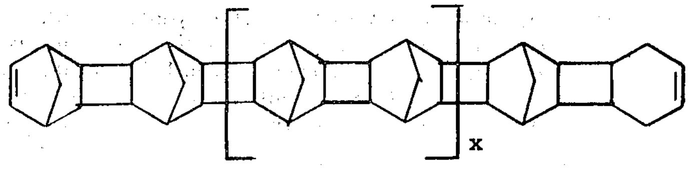

EXAMPLE 14

Bicyclo[2.2.1]hept-2-en-5-ylmethyl bicyclo[2.2.1]hept-2-en-5-carboxylate was prepared by the reaction of equimolar amounts of cyclopentadiene with acrolein to produce bicyclo[2.2.1]-hept-2-en-5-aldehyde followed by the Tischenko condensation thereof to the carboxylate. A solution of 6.5 grams of the carboxylate and 0.356 grams of acetophenone was prepared and irradiated for 309 hours at about 40°C. in a manner similar to that described in Example 13. The viscous reaction product was dissolved in 200 ml. of acetone and precipitated with methanol. The precipitate was filtered, redissolved in acetone and reprecipitated with methanol. The white polymer had a reduced viscosity of 0.03 at 30°C. when measured from a 0.2 per cent solution in chloroform. An ebulliscopic molecular weight determination in chloroform indicated a molecular weight of about 2120 ± 100. A film was produced from the polymer whose structure was confirmed by infrared analysis as being:

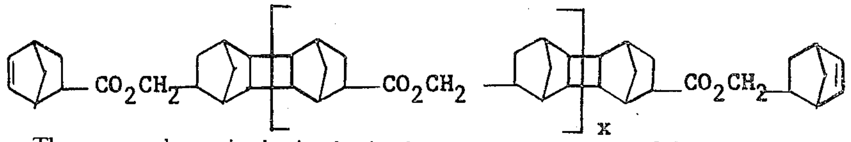

The same polymer is obtained using benzene, toluene or hexane as a solvent in the irradiation reaction.

EXAMPLE 15

A. A solution was prepared containing 20 grams of the carbamate of Example 1 and 1 gram of acetophenone in 20 ml. of benzene.

B. For comparison purposes, a solution of 20 grams of the polycaprolactone diol used as the starting reactant in Example 1 and 1 gram of acetophenone in 20 ml. of benzene was also prepared.

The two solutions, in separate sealed tubes, were irradiated for 161 hours at about 47°C. in a manner similar to that described in Example 13. The contents of Tube A completely gelled whereas the contents of Tube B showed no detectable change. The tubes were opened and distilled overnight under vacuum on a steam bath to remove the benzene solvent.

The polymer recovered from Tube A was a waxy solid that had a reduced viscosity of 0.167 at 30°C. when measured from 0.2 per cent solution in benzene. A film was produced from the polymer, whose structure was confirmed by infrared analysis as being repeating units of the formula:

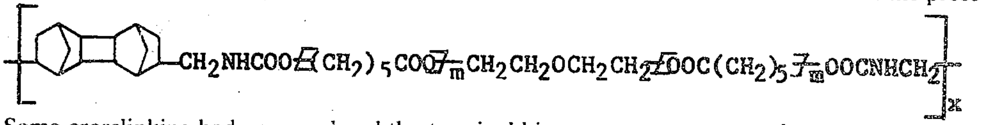

Some crosslinking had occurred and the terminal bicyclo groups had ring unsaturation.

The contents of Tube B after irradiation was unreacted polycaprolactone diol. The reduced viscosity was 0.094 as compared to 0.097 prior to irradiation. viscosity was determined at 30°C. using a 0.2 per cent solution in benzene. This experiment shows that the dinorbornene compounds polymerize whereas the polycaprolactone diol does not.

EXAMPLE 16

A mixture was prepared containing 29.7 grams of the carbamate of Example 2 and 1 gram of acetophenone. The mixture was irradiated for 269 hours at about 40°C. in a manner similar to that described in Example 13. The reaction product was dissolved in 100 ml. of benzene and 30 ml. of cyclohexane were added; two layers developed. The oil layer was separated and stripped on a rotary evaporator at 80°C. and 10.1 mm. pressure for two hours to remove volatiles. The clear, viscous residue had a reduced viscosity of 0.10 when measured from a 0.5 per cent solution in chloroform. Infrared analysis showed the presence of ladder polymer units of the formula:

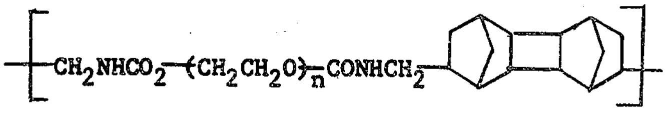

The terminal bicycloheptene units had ring unsaturation.

SECTION C

EXAMPLE 17

A high molecular weight polycaprolactone, having a reduced viscosity of 2.05 when measured at 25°C. using a 0.2 per cent solution in benzene, was milled with 5 per cent by weight of pentacyclo(8.2.1.$1^{4,7}$.$O^{2,9}$.$O^{3,8}$)tetradeca-5,11-diene until a uniform blend was obtained. No gross changes in the mechanical properties of the polycaprolactone were noted. A plaque having a diameter of five inches and a thickness of 20 mils was prepared. For control purposes a similar plaque was prepared from the same polycaprolactone. The two plaques were irradiated at 40°C. with a 100 watt medium pressure ultraviolet mercury arc lamp. At intervals sections were removed to observe the effect of the irradiation treatment. Initially, the ultraviolet irradiation caused a rapid decrease in the original molecular weight in both plaques; within two hours viscosity measurements indicated that the average molecular weight was only about one fourth of the original average value. However, as the irradiation continued the molecular weight of the plaque produced from the blend increased and after 20 hours of irradiation a maximum was reached. The resulting polymer was tough and flexible. The control plaque produced from the unmodified polycaprolactone continued to degrade and after 20 hours of irradiation the polymer was weak and brittle. The results show that the presence of the dinorbornene compound reversed the effect of ultraviolet radiation on polycaprolactone from that of predominantly degradation to that of predominantly crosslinking.

EXAMPLE 18

A uniform blend was prepared by milling polyethylene having a density of 0.96 gram per cubic centimeter and a melt index of 0.5 decigram per minute with 5 weight per cent of pentacyclo(8.2.$1^{4,7}$.$0^{2,9}$.$0^{3,8}$)tetradeca-5,11-diene as the dinorbornene compound. A five inch plaque, about 22 mils thick, was molded from the blend (Plaque I).

A second plaque was prepared from a blend containing 10 weight per cent of the same dinorbornene compound (Plaque II).

A third plaque was prepared from the unmodified polyethylene (Plaque III) without dinorbornene compound present.

The plaques were irradiated under nitrogen by one mev. electrons from a Van de Graaff accelerator and the amount of irradiation necessary for effective crosslinking was determined by determination of the amount of insoluble polymer. The amount of insolubilization was determined by refluxing a weighed portion of the irradiated plaque for four hours in ethylbenzene under nitrogen, draining and again extracting with refluxing ethylbenzene for one-half hour, drying at 60°C. in a vacuum oven overnight, and reweighing to determine the amount of insoluble crosslinked polymer remaining. It was fond that the dinorbornenyl compound enhanced the crosslinking reaction to the extent that gelation occurred in the blends after irradiation with from about 1.5 to 2 megarad; whereas, gelation occurred in the unmodified polyethylene only after irradiation with more than 3 megarads. The amount of insolubilization achieved at various radiation dosages is tabulated below. Eventually, at about 20 megarads, all of the plaques exhibit an insolubles of about 80 per cent. However, the rapid crosslinking achieved by the blend at lower dosages was completely unobvious and unexpected.

| Dose mergarads | Per Cent Insoluble Plaque I | Plaque II | Plaque III |
|---|---|---|---|
| 1.5 | 7.5 | — | — |
| 2.0 | 16 | 13 | 0 |
| 3.5 | 38 | 36 | 10 |
| 5.0 | 51 | 49 | 31 |
| 10.0 | 74 | 73 | 61 |

EXAMPLE 19

A uniform blend was prepared by milling poly-epsiloncaprolactone having a reduced viscosity of 2.05 dl/g, measured at 30°C. in a 0.2 per cent solution of the polymer in benzene, with 5 per cent by weight of the dinorbornene compound produced in Example 1. A portion of the blend was compression molded into a five inch diameter plaque having a thickness of 20 mils (Plaque I).

A second plaque was prepared from a uniform blend of the same poly-epsilon-caprolactone with 5 weight per cent of bicyclo[2.2.1]hept-2-en-5-ylmethyl bicyclo[2.2.1]hept-2-en-5-carboxylate (Plaque II).

A third plaque was prepared from a uniform blend of the same poly-epsilon-caprolactone with 20 weight per cent of the dinorbornene compound of Example 1 (Plaque III).

A fourth plaque was prepared from the unmodified polyepsilon-caprolactone for control and comparison purposes. (Plaque IV). It is known that high energy electons do not affect poly-epsilon-caprolactone and will not crosslink the unmodified polymer at the doses used below.

Two portions of each of Plaques I and II were cut and irradiated under nitrogen with one mev electrons from a Van de Graaff accelerator. One portion of each was treated with 4 megarads and the other portion with 8 megarads. The per cent insoluble in benzene at 60°C. and other properties were determined and compared with the properties of the control, Plaque IV. It was fond that crosslinking readily occurred as shown by a drop in melt index and increase in stiffness and yield stress; the tensile and elongation decreased. The results are summarized below:

| | Plaque I | | Plaque II | | Plaque IV |
|---|---|---|---|---|---|
| Dose, megarad | 4 | 8 | 4 | 8 | 0 |
| Stiffness, psi (ASTM-D-882) | 61,000 | 56,300 | 61,700 | 58,300 | 48,600 |
| Tensile, psi (ASTM-D-882) | 2,480 | 2,350 | 2,560 | 2,530 | 5,240 |
| Elongation, % (ASTM-D-882) | 126 | 23 | 135 | 55 | 700 |
| Yield stress, psi (ASTM-D-882) | 3,230 | 3,240 | 3,340 | 3,310 | 2,000 |
| Insoluble, % | 66.6 | 66.8 | 77.6 | 76.5 | 0 |
| Melt index, dgm/min (ASTM-D-1238-62T) | 0.128 | 0 | 0 | 0 | 2.1 |

Blends of polycaprolactone diols and poly(vinyl chloride) are known to stiffen with time, known as the aging effect, particularly at concentrations of about 30 weight per cent or more of the polycaprolactone in the blend. This is a decided disadvantage since polycaprolactone is an excellent plasticizer for poly(vinyl chloride). Until the present many unsuccessful attempts have been made to arrest the aging effect of such blends.

EXAMPLE 20

A uniform blend was prepared with 24 grams of polycaprolactone diol having a reduced viscosity at 25°C. of 1.48 when measured from a 0.2 per cent solution in benzene and 6 grams of the dinorbornene compound of Example 1 by blending on a heated two-roll mill. This blend contained 20 per cent by weight of the dinorbornene compound and was used as the masterbatch to prepare the following blends with poly(vinyl chloride).

A uniform blend was produced by blending 60 parts by weight of poly(vinyl chloride) having a reduced viscosity at 30°C. of about 0.98, measured from a 0.2 per cent solution in cyclohexane, with 40 parts by weight of the above-prepared masterbatch. The blend also contained 1.5 parts by weight of barium-cadmium laurate as heat stabilizer. Several plaques were pressed from the blend, each 5.25 inches in diameter and 25 mils thick (Plaques Series I).

One of the plaques was retained for control purposes and the other plaques were irradiated under nitrogen with one mev electrons from a Van de Graaf accelerator at different dosages. The stiffness modulus on all of the plaques was then determined over a total period of 88 days after irradiation. The irradiaton dosages used and results obtained are tabulated below:

| | Series I Plaques Control | a | b | c | d |
|---|---|---|---|---|---|
| Irradiation dosage, mrads. | 0 | 0.22 | 0.43 | 2.2 | 4.3 |
| Stiffness modulus, psi after 3 days | 1,340 | 1,100 | 1,270 | 1,240 | 1,220 |
| 4 | 1,280 | 1,180 | 1,400 | 1,400 | 1,310 |
| 7 | 1,330 | 1,090 | 1,340 | 1,260 | 1,110 |
| 7 | 1,880 | 1,390 | 1,390 | 1,390 | 1,300 |
| 24 | 2,180 | 1,390 | 1,420 | 1,490 | 1,460 |
| 33 | 2,570 | 1,500 | 1,550 | 1,510 | 1,330 |
| 55 | 3,620 | 1,600 | 1,490 | 1,520 | 1,390 |
| 88 | 5,100 | 1,780 | 1,640 | 1,620 | 1,650 |
| Color | Clear | Clear | Clear | Light Brown | Light Brown |

A second blend was produced by uniformly blending 55 parts of the poly(vinyl chloride) with 45 parts of the masterbatch and plaques were pressed from this second blend (Plaques Series II).

The plaques of Series II were irradiated and tested by the same procedures used for the plaques of Series I. The results are tabulated below:

| | Series II Plaques Control | a | b | c | d |
|---|---|---|---|---|---|
| Irradiation dosage, mrads. | 0 | 0.22 | 0.43 | 2.2 | 4.3 |
| Stiffness modulus, psi after 3 days | 1,400 | 860 | 840 | 1,040 | 940 |
| 4 | 1,790 | 880 | 900 | 1,070 | 850 |
| 7 | 2,670 | 990 | 940 | 1,030 | 860 |
| 17 | 5,570 | 1,360 | 1,020 | 1,190 | 1,040 |
| 24 | 7,130 | 1,980 | 1,230 | 1,310 | 1,070 |
| 33 | 7,730 | 2,400 | 1,090 | 1,290 | 1,110 |
| 55 | 9,890 | 3,490 | 1,390 | 1,220 | 1,180 |
| 88 | 13,400 | 6,000 | 1,500 | 1,300 | 1,430 |
| Color | Clear | Clear | Clear | Light Brown | Light Brown |

A third blend was produced by uniformly blending 50 parts of the poly(vinyl chloride) with 50 parts of the masterbatch and plaques were pressed from this third blend (Plaques Series III). These blends generally stiffen quite rapidly and one can usually feel the change in stiffness by hand flexing a sample that has aged overnight at room temperature.

| | Series III Plaques Control | a | b | c | d |
|---|---|---|---|---|---|
| Irradiation dosage, mrads. | 0 | 0.22 | 0.43 | 2.2 | 4.3 |
| Stiffness modulus, psi after 3 days | 11,700 | 7,400 | 3,900 | 720 | 700 |
| 4 | 13,300 | 8,930 | 4,720 | 780 | 730 |
| 17 | 12,800 | 9,400 | 4,760 | 830 | 820 |
| 17 | 18,400 | 12,600 | 7,000 | 1,420 | 1,140 |
| 24 | 23,800 | 16,300 | 7,930 | 1,800 | 1,620 |
| 33 | 22,000 | 15,200 | 8,200 | 2,090 | 1,600 |
| 55 | 18,900 | 15,200 | 9,030 | 2,290 | 1,910 |
| 88 | 24,700 | 18,300 | 11,400 | 3,400 | 2,480 |
| Color | Clear | Clear | Clear | Light Brown | Light Brown |

The lower stiffness modulus values of the irradiated blends is an indication that the aging effect does not occur to the extent that it does in the blends that have not been irradiated. It was not obvious that this improvement could be achieved by this method.

EXAMPLE 21

A uniform blend was produced by roll milling 6 grams of the same polyvinyl chloride used in Example 20, 4 grams of the dinorbornene compound of Example 1 and 0.09 gram of a bariumcadmium laurate stabilizer. Plaques, five inches in diameter and 0.02 inch thick, were molded at 140°C. and 1,000 psi pressure from the blend. Portions of the plaques were irradiated under nitrogen by one mev electrons from a Van de Graaff accelerator. The extend of crosslinking was determined by extracting with ethylene dichloride at 60°C. for four days, removing the solvent, and extracting for another two days at 60°C. The residue was dried and the per cent insoluble calculated. The results are tabulated below:

| Sample | Irradiation dose, mrad | Insolubles, % |
|---|---|---|
| Control | 0 | 0.42 |
| a | 0.1 | 0.70 |
| b | 0.2 | 22.25 |
| c | 0.5 | 65.21 |
| d | 1.0 | 80.00 |
| e | 2.0 | 88.48 |
| f | 4.0 | 93.54 |

At these dosages poly(vinyl chloride) is known not to crosslink and gel.

EXAMPLE 22

Uniform blends were produced by blending 100 parts of polyethylene oxide having an average molecular weight of about 600,000 with 5 parts of the dinorbornene compounds specified below. The blends were molded into plaques, each five inches in diameter and from 0.01 to 0.015 inch thick; a control plaque of the unmodified polyethylene oxide was also produced. The plaques prepared from the blends were exposed to a 100 watt medium pressure mercury arc lamp at a distance of four inches for 25 hours on each side. The extent of crosslinking was determined as described in Example 21, using acetonitrile as the extraction solvent.

The unmodified polyethylene oxide control sample had a 13.75 per cent insolubles content.

The blend with 5 parts per hundred of the dinorbornene compound of the formula:

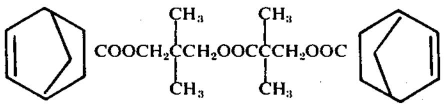

had a 56.4 per cent insolubles content after irradiation.

The blend with 5 parts per hundred of bicyclo[2.2.1]hept-2-en-5-ylmethyl bicyclo[2.2.1]hept-2-en-5carboxylate had a 68.8 per cent insolubles content after irradiation.

The blend with 5 parts per hundred of the dinorbornene compound of the formula:

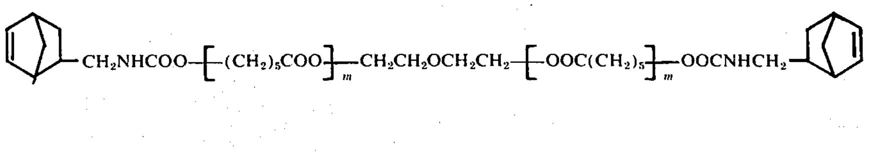

had a 47.6 per cent insolubles content after irradiation.

EXAMPLE 23

A solution was prepared containing 0.4 gram of a nonionic surfactant (the nine mole adduct of ethylene oxide to one mole equivalent of a mixture of $C_{11}$ to $C_{15}$ linear alcohols) 40 grams of bicyclo[2.2.1]hept-2-en-5-ylmethyl bicyclo[2.2.1]hept-2-en-5-carboxylate and 360 grams of acetone. A printed cotton fabric was padded with the solution and passed through a wringer to ensure a six weight per cent pick up of the bicycloheptene compound. The treated fabric was dried at 150°F. for five minutes and then irradiated with two mev electrons from a Van de Graaff accelerator to impart a total dose of 2 megarads. The irradiated fabric was washed, tumble-dried and subjected to the known standard Monsanto Dry Crease Recovery Test. The treated cellulosic cotton fabric had a crease recovery of 197° compared to 180° for the untreated cotton fabric, which is considered a decided improvement. This experiment illustrates that the dinorbornene compounds, the polymers thereof, and blends of both with other polymers can be used to improve the crease resistance of fabrics. It also shows that cellulose, a natural polymer, can be crosslinked therewith.

In a similar manner a series of crosslinkable blends are produced by blending 100 parts of the following polymers with 5 parts of the indicated dinorbornene compound.

| Polymer | Dinorbornene Compound |
|---|---|
| Polypropylene | 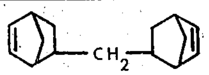 |
| Poly(ethylene/norbornadiene) | 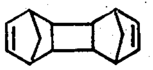 |
| Poly(ethylene/propylene/5-ethylidenebicyclo[2.2.1]-hept-2-ene) | Dinorbornene carbamate of Example 1 |
| Poly(ethylene/acrylic acid) | Dinorbornene carbamate of Example 3 |
| Poly(ethylene/vinyl acetate) | Dinorbornene diester of Example 7 |
| Poly(ethylene/ethyl acrylate) | Dinorbornene diester of Example 11 |
| Poly(vinylidene chloride) | Dinorbornene carbamate of Example 9 |
| Poly(vinyl acetate) | 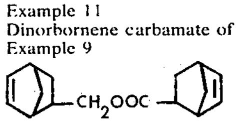 |
| Poly(acrylic acid) | Polymer of Example 13 |
| Polyacrolein | 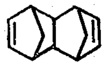 |
| Polyacrylonitrile | Polymer of Example 15 |
| Poly(ethylene glycol terephthalate) | Dinorbornene urea of Example 9 |
| Ethylene oxide-propylene oxide adduct of glycerol-M.Wca. 4000 | Polymer of Example 14 |
| Polyurethane | Polymer of Example 16 |
| Methyl cellulose | Dinorbornene amide of Example 10 |

Similarly blends are produced using 10, 20, 30 or 50 parts of the dinorbornene compound for each 100 parts of polymer.

What is claimed is:

1. A dinorbornene of the formula:[BCH-X-$G_n$-poly-(alkylenecarbonyloxy)alkylene]$_2$O wherein BCH is the bicycloheptenyl group; X is a divalent alkylene of from 1 to 8 carbon atoms; G is a divalent carbamoyloxy group; and $n$ is an integer having a value of 0 or 1.

2. The compound as claimed in claim 1 of the formula:

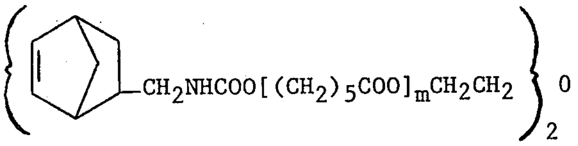

wherein $m$ has an average value of about 16.6.

3. The compound as claimed in claim 2 wherein $m$ has an average value of about 83.

* * * * *